Figure 1:
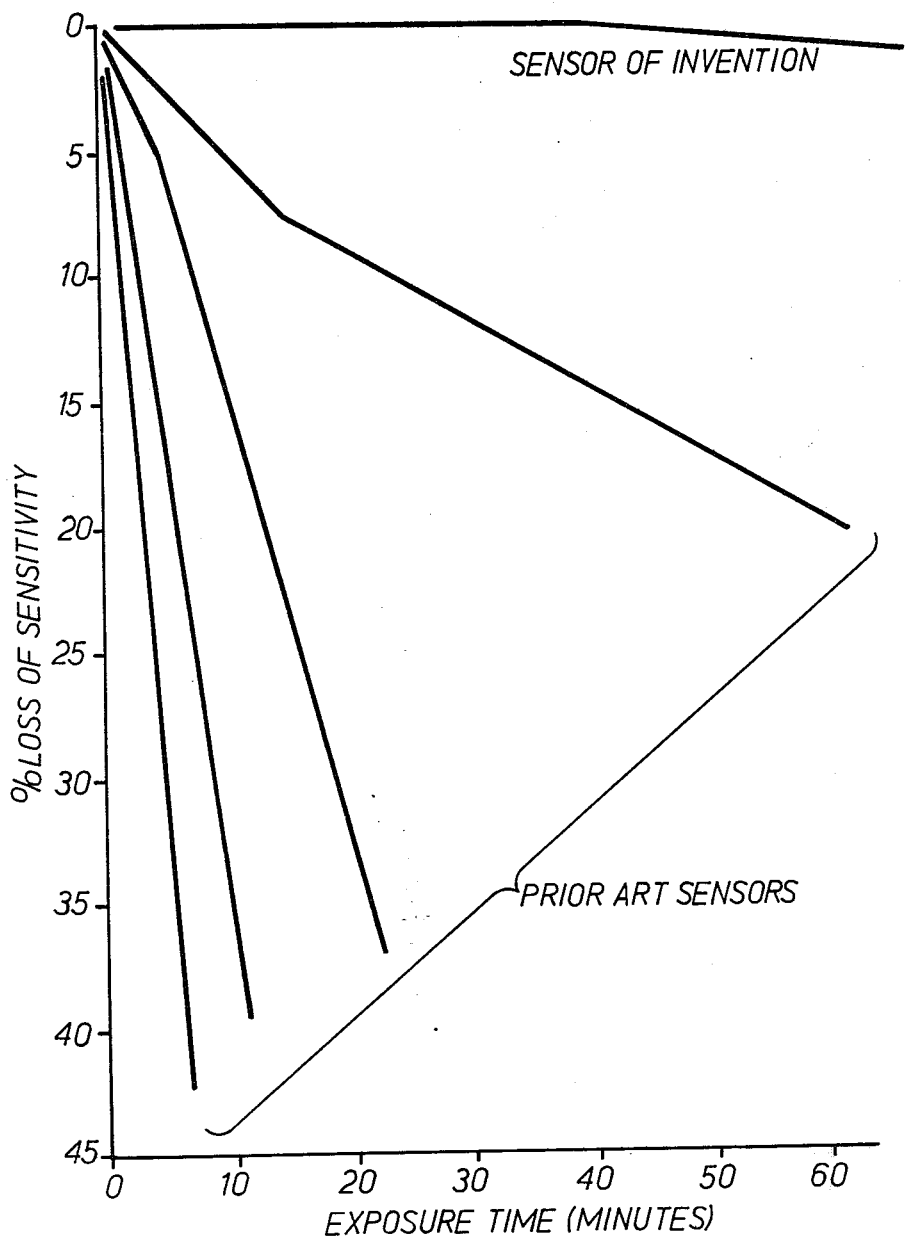

United States Patent [19]

Sonley

[11] 4,303,612

[45] Dec. 1, 1981

[54] GAS SENSITIVE DEVICES

[75] Inventor: John M. Sonley, Cobham, England

[73] Assignee: Diffracto Ltd., Windsor, Canada

[21] Appl. No.: 156,386

[22] Filed: Jun. 4, 1980

Related U.S. Application Data

[63] Continuation of Ser. No. 17,274, Mar. 5, 1979, abandoned.

[30] Foreign Application Priority Data

Mar. 8, 1978 [GB] United Kingdom ............... 9226/78

[51] Int. Cl.$^3$ ............................................. G01N 27/16
[52] U.S. Cl. ......................................... 422/94; 73/23;
422/97
[58] Field of Search ................................... 422/94–98,
422/119, 90; 338/23, 25; 73/23, 27

[56] References Cited

U.S. PATENT DOCUMENTS

| 3,200,011 | 8/1965 | Baker | 422/94 |
| 4,045,177 | 8/1977 | McNally | 422/96 |
| 4,111,658 | 9/1978 | Firth et al. | 422/98 |
| 4,123,225 | 10/1978 | Jones | 422/98 |

Primary Examiner—Michael S. Marcus
Attorney, Agent, or Firm—Larson and Taylor

[57] ABSTRACT

Catalytic gas sensors comprise a noble metal filament onto which is applied alumina having a particle size of not greater than 100 Å and a catalyst material is impregnated into the dried alumina. The alumina may be dried by passage of an electric current through the filament and, prior to coating the filament may be stabilized by coating with a thermally decomposable aluminium salt and decomposed by passing a pulsed electric current.

7 Claims, 2 Drawing Figures

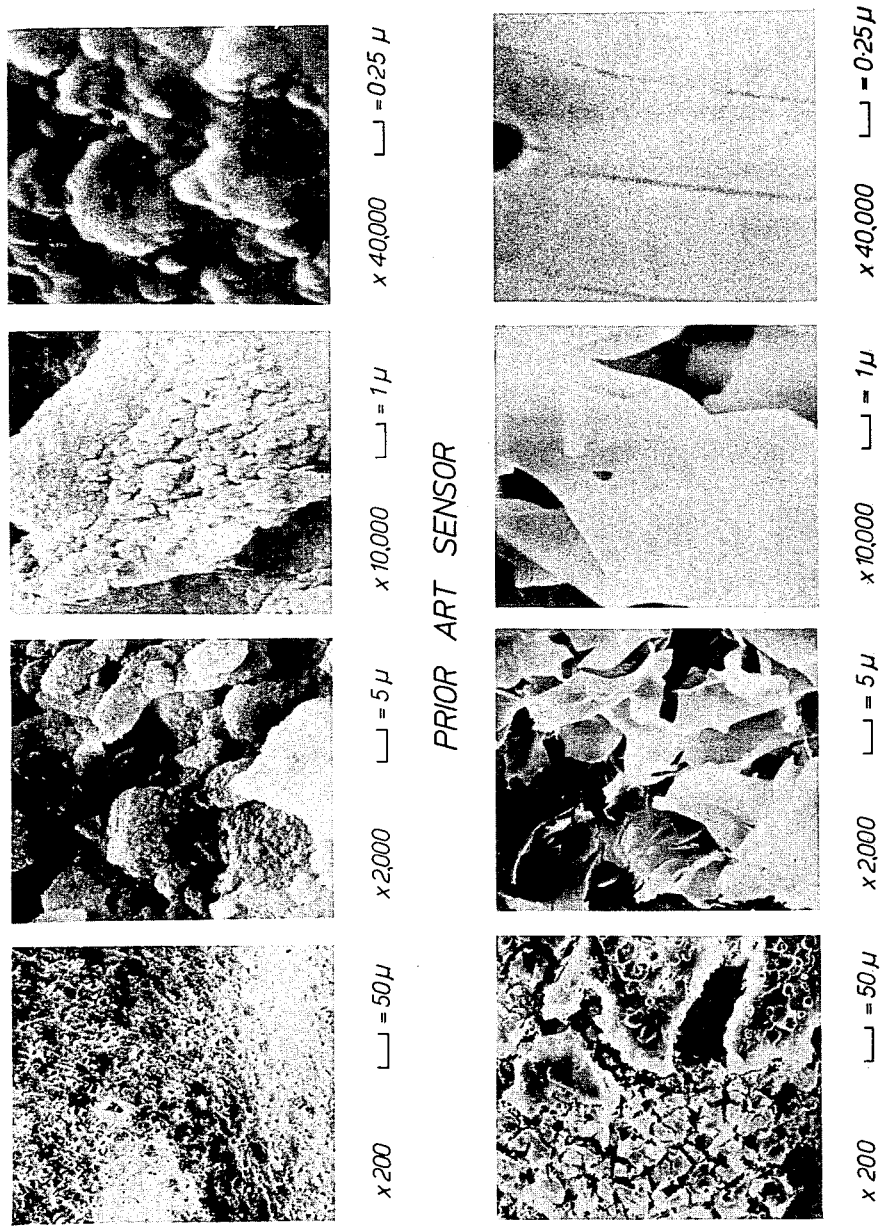

GAS SENSITIVE DEVICES

This is a continuation of application Ser. No. 17,274 filed Mar. 5, 1979 now abandoned.

This invention relates to the detection of gases. More particularly, the invention relates to gas sensitive devices or gas sensitive elements employed for the detection of gaseous hydrocarbons, such as methane in a mixture with air, and the method of preparation of the device in a pellistor form.

The use of catalysts for detecting and measuring methane concentrations in air is very well known. For example, in our prior U.K. Pat. No. 1,447,488, there is described apparatus for detecting the presence of natural gas in air and the level of concentration of the gas. In such apparatus, the catalyst is formed into a pellistor which, in turn, forms a resistance in one arm of the Wheatstone bridge. The electrical resistance of the pellistor varies as a function of the concentration of hydrocarbon in contact with the catalyst material and the functional variation is measured and shown on a meter indicating the concentration.

Previous work, involving the deposition of thin layer of catalyst on the surface of a chemically deposited alumina substrate produced a catalyst of poor resistance to poisoning (as tested in a 5 ppm Hexamethyl disiloxane in 30% LEL (Lower Explosive Limit) methane mixture. Although it was apparent that sufficient palladium was present on the surface of the sensor, it appeared probable that only a limited number of active sites were available for reaction.

A gas sensitive device was described in U.K. Pat. No. 892,530 (National Research Development Corporation) wherein the device was formed by coiling a filament of a noble metal from the platinum group, for example platinum or an alloy of platinum, and embedding the coil within or completely surrounded by an oxide or other refractory materials such as alumina or silica, so as to form a pellet around the filament. The alumina or silica is applied to the filament by the evaporation and decomposition by heat of an aqueous paste or solution of a compound such as aluminium nitrate or aluminium hydroxide. The decomposition by heat is effected by passing an electric current through the filament. The gas sensitive device is completed by including a layer of a catalyst such as palladium or a mixture of platinum and palladium to the outer surface of the aluminia by applying the catalyst as a solution or dispersion of a compound or compounds of one or more metals of the platinum group.

The present invention proposes a gas detector and more particularly a gas sensitive device for use as a pellistor which has a high resistance to poisoning.

According to the invention there is provided a catalytic gas sensing element comprising a noble metal filament having a porous coating of alumina which coating is impregnated with a material which catalyses the oxidation of hydrocarbons and is formed by applying a slurry of alumina onto the filament, drying the applied slurry, applying a solution of the catalytic material to the dried alumina, and drying the thus impregnated alumina, and wherein the particle size of the alumina, in at least the outer regions of the coating, is not more than 100 Å.

The gas sensitive device may be prepared by the steps including which winding the platinum coil made from thermopure platinum wire, applying separate coats of saturated aluminium nitrate, at least two of the coats being decomposed by a pulsed electrical energy source, applying a mixture of gamma alumina and aluminium nitrate as a smooth paste to the coated platinum coil, by applying the alumina slurry with a glass rod, applying a catalyst to the alumina bead, drawing the catalyst solution upon the bead, and exposing the bead in a mixture of natural gas and air to condition the gas sensitive device.

According to the invention there is also provided a gas detector, including a gas sensitive device incorporated in one arm of a Wheatstone Bridge wherein the gas sensitive device comprises a coil of platinum wire coated with alumina and a catalyst.

An example of the gas detector is the one described in our U.K. Pat. No. 1,447,488.

It is envisaged that it is within the scope of the invention to provide a gas sensitive device that can be included in a fixed or portable gas detector.

Prior to coating with the alumina which is the support for the catalytic material, the filament, which may be in the form of a coil of noble metal wire, is preferably stabilised by chemically depositing a first coating of alumina. The stablised filament may then be mounted and spot-welded to the main pellistor support.

The alumina slurry to be used for the filament stabilisation and for the coating is in the form of a smooth paste comprising alumina, preferably gamma-alumina, and an aqueous binder. The bulk volume ratio of alumina to aqueous binder preferably ranges from 1 to 3:1. Additionally, the alumina may contain up to 0.6% by eight of sulphate ion .

The particle size of the alumina should not be greater than 100 Å and preferably angles from 50–70 Å. The particles comprising the alumina may be discrete single particles or may be in the form of a conglomerate of sub-particles. Particles formed as conglomerates and having an average particle size of not greater than 100 Å are preferred since they have a larger surface area than a similarly sized single particle and have a greater resistance to poisoning.

The aqueous binder may be water but desirably is a dilute aqueous solution of a decomposable aluminium salt, e.g. a less than 2% by weight solution of aluminium nitrate. The coating may be dried by passing a current of from 20–30 mA, preferably about 25 mA, for a period of from 0.5–2.0 hours, preferably about 1.0 hours. The heating effect caused by the passage of electrical current maintains the temperature of the coated filament at about ambient temperature to produce a hard dry pellet.

The above coating may include one or more coats.

Prior to the above, the platinum coil is stabilized by chemically decomposing aluminium nitrate onto the filament. The stabilised filament is then mounted onto the pellistor support.

The initial coating step may include one or more coats of thermally decomposed aluminium nitrate and is produced by passing a current of between 0.1 and 0.5 amps for a period of 1–10 seconds and then pulsing it with an electric current through the coating with a 1–10 volt charge from a 5,000–20,000 microfarad capacitor bank.

A coating of an alumina slurry, as previously described, is applied to the stabilised filament, to form a bead measuring typically 2.0 mm by from 1.5 to 2.3 mm.

The catalyst support coating is then dried, preferably according to the technique described for the stabilising coating.

After the support has been dried, the catalytic material is applied to the support. The catalyst is any material which catalyses the oxidation of hydrocarbons, e.g. methane. Examples of such catalytic materials are noble metals such as platinum, palladium or nitrates thereof. The catalytic material may be applied to the support by conventional deposition techniques, for example, by impregnating the support with a solution of the catalyst metal such as a chloroplatinate.

After impregnation, the pellistor bead is dried. The first drying step (at constant current) is carried out as described for the drying of the alumina stabilising and support coatings. However, the second drying step is preferably carried out by heating the initially dried bead at a rate of from 3–5 mA/min. to a final current value of from 300–500 mA/min. say about 400.

After this final drying stage, the catalyst may be activated prior to use by exposure to a reducing atmosphere, e.g. a mixture of natural gas and air. However, prior to activation, the catalyst sensor may be coated with a further coating of alumina, applied as hereinbefore described. In this case, no catalyst impregnation is carried out.

Since the pellistor forms part of the Wheatstone Bridge, a reference electrode having a known variation of resistivity with temperature can be prepared in a similar manner to the pellistor except that no catalytic material is applied. However, it has been observed that alumina, which is coated in accordance with the invention, has some catalytic activity. Thus, it may be desirable to coat the reference electrode with glass.

The present invention will be described in greater detail with reference to the following Example, and the accompanying drawing and photograph, in which:

FIG. 1 is a graph showing the percentage loss of sensitivity of the pellistor with exposure to time in an atmosphere comprising 5 ppm hexamethyl disiloxane in 30% LEL (methane/air), compared to known pellistors, and FIG. 2 is a photograph showing a comparitive surface of a gas sensitive device according to the present invention and a surface of a known device.

Preparation of the pellistor in accordance with the invention will be described as an example.

A 10½ turns platinum coil is wound using a 0.5 mm thermopure platinum wire (resistance 47 ohms/meter) the coil is attached to electrodes of a dipping vessel and is coated wih two coats of aluminium nitrate which are evaporated and decomposed on the coil at a current of 0.24 amps for one minute. These first two coats are followed by a further two coats which are evaporated onto the coil and the first two layers for five seconds at a constant current of 0.3 amps and then pulsed with a seven volt charge from an 11,600 microfarad capacitor bank. The decomposition produced by the high energy discharge is important and is accompanied by noticeable increase in the volume of the element. These four initial coats perform two main duties which (a) to stabilise the geometry of the platinum coil, (b) to form a firm but highly porous basis for the subsequent coats.

A 50–70 angstrom gamma alumina is ground with 1% aluminium nitrate aqueous in an agate pestle and mortar to a smooth paste. The platinum coil with the four coats as described above, is spot-welded onto a header which carries the coil and leads from the coil are connected to a pulsed energy unit. One large drop of the alumina slurry is applied with a glass rod to the bead to form a smooth round droplet of about 2 mm across its diameter. 50 mA is passed through the coil and a 15 minute drying time in warm atomsphere is allowed. The current is then switched off.

To the surface of the now white alumina bead is applied a glass rod moistened with a catalyst comprising of palladium and thorium dioxide. The rod is left in contact with the bead until the latter has "soaked up" the catalyst solution and left the outer surface shiny. A fan is switched on which has a velocity of 0.5 to 1.5 m per second of air, and the products of decomposition are blown away from the surface of the gas sensitive device to avoid corrosion of the support wires.

The catalyst solution around the coil and nitrate layers is dried for 5 minutes at 100 milliamps current and then the current is increased slowly over a period of 10 minutes up to 400 mA with particular attention to slow increases between the currents of 200 and 300 mA. Finally, with a current of 350 mA the sensor is exposed to 13% natural gas in air for 15 seconds to condition the sensor. The current is then switched off.

The prepared sensing device is then placed inside a can for protection, upon which the gas sensitive device is ready for use.

It has now been proved by tests on the gas sensitive device according to the present invention that the loss in sensitivity when exposed to poisons in air has been greatly reduced compared to known pellistors and can be seen in the attached graph.

It is believed that the resistance of the gas sensitive device according to the present invention to poisoning by the atmosphere is due to the increase in volume the device achieves during the process stage particularly the pulsing of electrical energy during drying and conditioning of the deposited alumina and during decomposition of the aluminium nitrate component of the coatings. This, it is believed, leads to a greater avaiblable surface area of catalyst and therefore a greater area for resistance of the catalyst to poison.

A further important feature of the invention is the conditioning step of allowing the catalyst precursor to be exposed to a 13% natural gas and air mixture for 15 seconds as current of 200–300 mA are passed through the coil.

It is shown from the electron microscopic photographs that the surface of the gas sensitive device of the present invention shows pore sizes ranging from $0.1\mu$ aggregating to $10\mu$ whilst in the photograph of known devices the surface shows a larger structure void of active catalysts sites.

What is claimd is:

1. A catalytic gas sensing element comprising a noble metal filament having a porous coating of alumina which coating is impregnated with a material which catalyses the oxidation of hydrocarbons wherein said element is formed by applying a slurry of alumina onto the filament, drying the applied slurry, applying a solution of the catalytic material to the dried alumina, drying the thus impregnated alumina and activating the catalytic material, wherein the particle size of the alumina, in at least the outer regions of the coating, is not more than 100 Å and wherein the alumina contains up to 0.6% by weight of sulphate ions present in at least the outer regions of the coating.

2. An element as claimed in claim 1 wherein the alumina particles are conglomerates formed from smaller particles, the average size of said conglomerate being not greater than 100 Å.

3. An element as claimed in claim 1 wherein the particle size is from 50–70 Å.

4. An element as claimed in claim 1 wherein there is a further coating of alumina on the catalyst impregnated coating.

5. An element as claimed in claim 1 wherein the filament is a stabilised filament produced by coating the noble metal with aluminium nitrate and decomposing the nitrate.

6. An element as claimed in claim 1 wherein the catalyst material is selected from platinum and palladium.

7. An element is claimed in claim 1 wherein the alumina is gamma-alumina.

* * * * *